(12) United States Patent
Shimizu et al.

(10) Patent No.: US 7,214,182 B2
(45) Date of Patent: May 8, 2007

(54) WIRELESS IN-VIVO INFORMATION ACQUIRING SYSTEM, BODY-INSERTABLE DEVICE, AND EXTERNAL DEVICE

(75) Inventors: Hatsuo Shimizu, Tokyo (JP); Kazutaka Nakatsuchi, Tokyo (JP)

(73) Assignee: Olympus Corporation, Tokyo (JP)

( * ) Notice: Subject to any disclaimer, the term of this patent is extended or adjusted under 35 U.S.C. 154(b) by 33 days.

(21) Appl. No.: 10/828,413

(22) Filed: Apr. 20, 2004

(65) Prior Publication Data
US 2004/0215083 A1    Oct. 28, 2004

(30) Foreign Application Priority Data
Apr. 25, 2003   (JP)   ............... 2003-122801

(51) Int. Cl.
*A61B 1/00*   (2006.01)
*A61B 1/04*   (2006.01)
(52) U.S. Cl. ...................... 600/117; 600/103
(58) Field of Classification Search ............... 600/109, 600/118, 160, 476
See application file for complete search history.

(56) References Cited

U.S. PATENT DOCUMENTS

| | | | | |
|---|---|---|---|---|
| 5,604,531 A | * | 2/1997 | Iddan et al. ............ 348/76 |
| 5,755,748 A | * | 5/1998 | Borza ..................... 607/61 |
| 6,045,527 A | * | 4/2000 | Appelbaum et al. .......... 604/22 |
| 6,194,996 B1 | * | 2/2001 | Okazaki et al. ............. 370/482 |
| 6,476,993 B1 | * | 11/2002 | Aoki ......................... 360/64 |
| 2001/0051766 A1 | * | 12/2001 | Gazdzinski .............. 600/309 |
| 2002/0177884 A1 | * | 11/2002 | Ahn et al. .................. 607/61 |

FOREIGN PATENT DOCUMENTS

JP    2001-231186    8/2001

\* cited by examiner

*Primary Examiner*—Roy D. Gibson
*Assistant Examiner*—Philip R Smith
(74) *Attorney, Agent, or Firm*—Scully, Scott, Murphy & Presser P.C.

(57) ABSTRACT

A pill inserted into a body of a patient acquires in-vivo information on the body of the patient. A receiver disposed on the outside of the body receives the in-vivo information on the body of the patient from the pill through an antenna. When a power supply signal is transmitted from the receiver to the pill through the antenna, a drive control signal for making the pill to execute a predetermined function is superposed on the power supply signal, which makes it possible to control various functions performed by the pill from outside.

14 Claims, 6 Drawing Sheets

WIRELESS IN-VIVO INFORMATION ACQUIRING SYSTEM, BODY-INSERTABLE DEVICE, AND EXTERNAL DEVICE

BACKGROUND OF THE INVENTION

1) Field of the Invention

The present invention relates to a wireless in-vivo information acquiring system, a body insertable device, and an external device.

2) Description of the Related Art

In the field of endoscopes, swallowable capsule-type endoscopes (hereinafter, "pill") have been on the market in recent years. The pill includes an imaging function and a wiring function. The pill has a mechanism such that the pill is swallowed by a patient for observation (diagnosis), travels along the inside of organs of the patient such as stomach and small bowel due to peristalsis of the organs, and successively imaging the inside of the organs in an observation period since the pill is swallowed until it is naturally excreted from the body of the patient.

In the observation period by the travel of the pill along the inside of the organs, data for images captured by the pill inside the body is successively transmitted to the outside through wireless communications, and the data is stored on a memory. By carrying a receiver including such a wireless communication function and a memory function, the patient can act freely during the observation period since the pill is swallowed until it is excreted. After the observation, a doctor or a nurse displays the image of the organs based on the image data stored on the memory and performs diagnosis.

As for a supply of the power, there are systems such as a battery supply system in which a battery is incorporated in this type of pill, because the pill remains inside the body of the patient, and supplies power to the inside of the pill, and a power transmission system that supplies power to the inside of the body by transmitting the power from the outside of the body of the patient to the pill.

The latter case of the power transmission system has a configuration in which a power receiving antenna is provided in the inside of the pill and power is transmitted to the inside of a radio capsule (corresponding to the pill) through the power receiving antenna to operate the radio capsule remaining in the body of the patient for a long time (see Japanese Patent Application Laid Open No. 2001-231186)

As this type of pill at present, there are M2A (trademark) produced by Given Imaging Ltd. of Israel and NORIKA (trademark) produced by Kabushiki Kaisha RF of Japan, which have already entered into its practical stage.

As explained above, the conventional power transmission system only supplies power from the outside of the body, and therefore, the operation of the pill cannot be controlled from the outside of the body. Since the pill itself consumes power constantly under any circumstances, a predetermined level or more power should be continuously transmitted thereto.

SUMMARY OF THE INVENTION

It is an object of the present invention to solve at least the problems in the conventional technology.

The wireless in-vivo information acquiring system according to one aspect of the present invention includes a body-insertable device that is inserted into a body of a patient, and an external device that is disposed on outside of the body of the patient. The external device includes a power source that outputs a power-supply signal for supplying power to the body-insertable device, a power supply signal transmitting unit that wirelessly supplies the power supply signal from the power source to the body-insertable device, and a control signal superposing unit that superposes a drive control signal on the power supply signal from the power source. The body-insertable device includes a function executing unit that executes a predetermined function to acquire in-vivo information on the body of the patient, and a control signal detecting unit that detects the drive control signal superposed on the power supply signal, and controls the function executing unit based on the drive control signal detected.

The body-insertable device according to another aspect of the present invention includes a function executing unit that executes a predetermined function to acquire in-vivo information on the body of the patient, a power-supply signal receiving unit that receives a power-supply signal wirelessly transmitted from outside as a power for driving the function executing unit, the power-supply signal including drive control signal superposed, a control signal detecting unit that detects the drive control signal superposed on the power supply signal received, and controls the function executing unit based on the drive control signal detected.

The external device according to still another aspect of the present invention includes a power source that outputs a power-supply signal for supplying power to a body-insertable device that is inserted into a body of a patient to execute a predetermined function, a control signal superposing unit that superposes a drive control signal for controlling the predetermined function of the body-insertable device on the power supply signal from the power source, and a power supply signal transmitting unit that wirelessly supplies the power supply signal from the power source to the body-insertable device that is inserted into the body, the power-supply signal including the drive control signal superposed.

The other objects, features, and advantages of the present invention are specifically set forth in or will become apparent from the following detailed description of the invention when read in conjunction with the accompanying drawings.

DETAILED DESCRIPTION

Exemplary embodiments of the present invention are explained in detail below with reference to the accompanying drawings.

Figure 1:
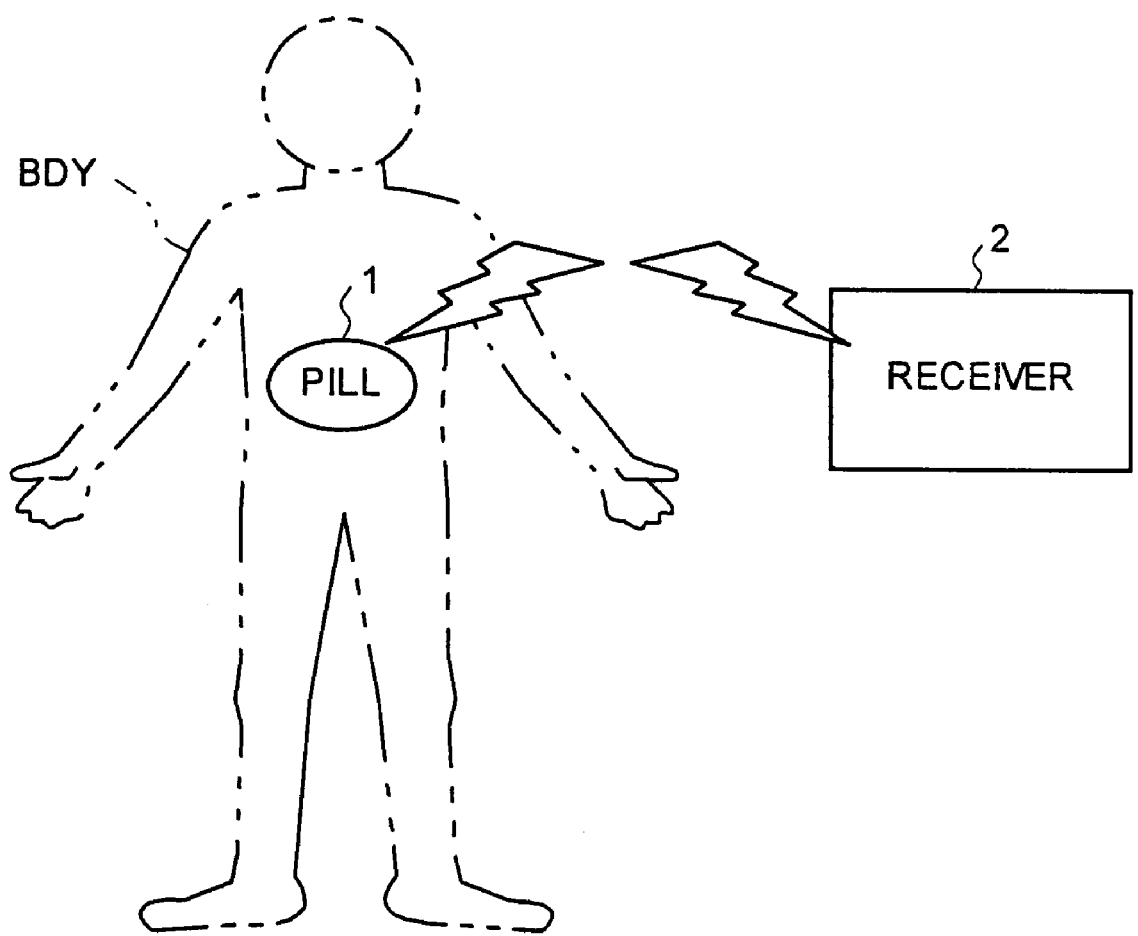
FIG. 1 is a schematic of a capsule-type endoscope system as an example of a wireless in-vivo information acquiring system according to the present invention.

FIG. 1 is a schematic of a capsule-type endoscope system as an example of a wireless in-vivo information acquiring system according to the present invention. The capsule-type endoscope system includes a pill (body-insertable device) 1 that is insertable into a body BDY of a patient, and a receiver 2 as an external device that is provided outside the body and wirelessly communicates various pieces of information with the pill 1.

Figure 2:
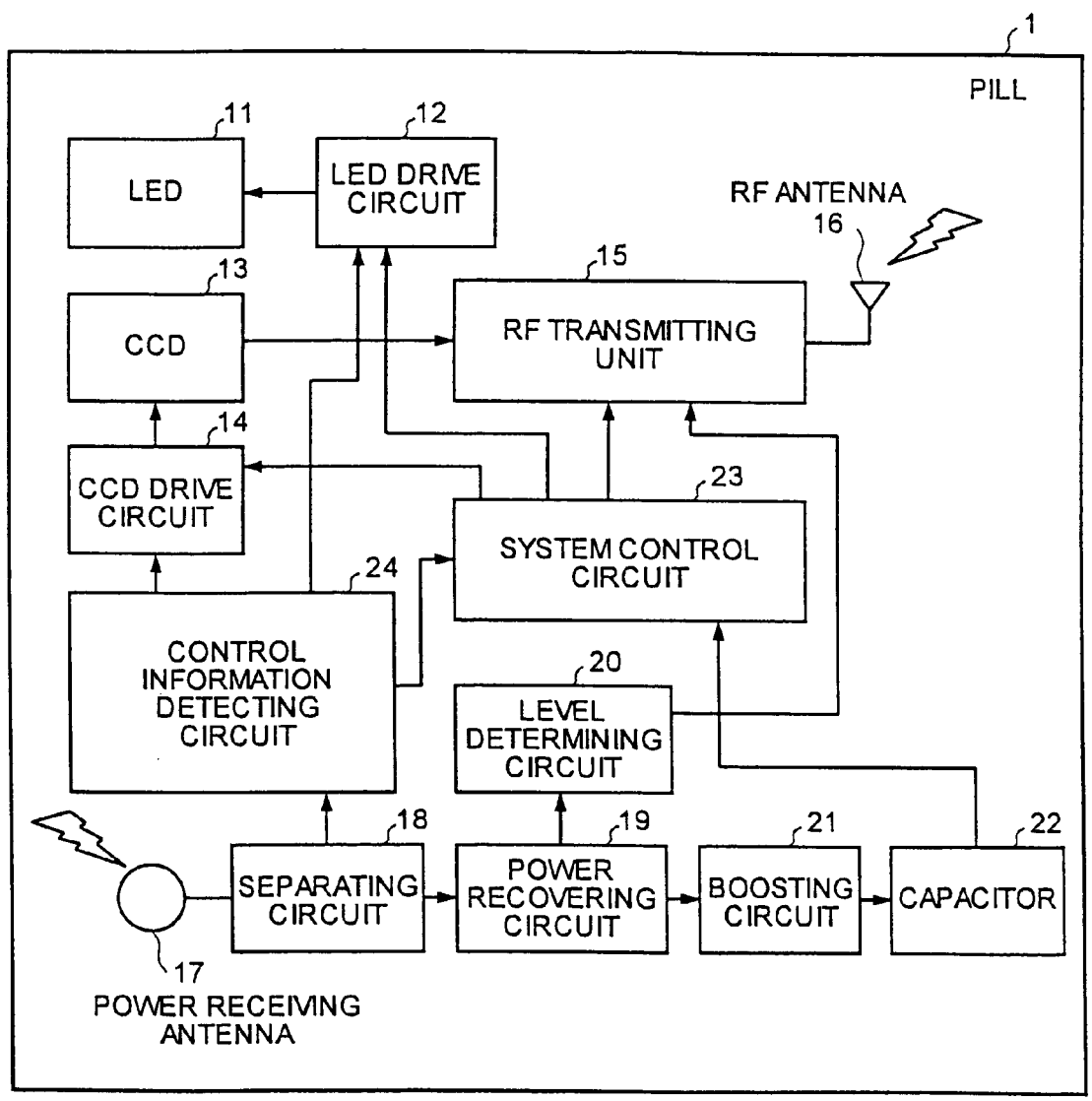
FIG. 2 is a block diagram of a pill according to an embodiment of the present invention.

FIG. 2 is a block diagram of a pill according to an embodiment of the present invention. As shown in FIG. 2, the pill 1 is the body-insertable device that is insertable into the body BDY of a patient. The pill 1 includes a light emitting diode (LED) 11 (function executing unit, illuminating unit) as a light emitting element that emits illumination light for illuminating a portion to be diagnosed of the body BDY of the patient, an LED drive circuit 12 that sends out an LED drive signal for driving the LED 11, a charge coupled device (CCD) 13 (function executing unit, sensor, imaging unit) that captures images of the body of the patient obtained by the illumination light, emitted from the LED 11, reflected from the portion to be diagnosed, a CCD drive circuit 14 that drives the CCD 13, a radio frequency (RF) transmitting unit 15 (function executing unit) that modulates an imaging signal output from the CCD 13 to an RF signal, and an RF antenna 16 that is a transmitting antenna for wirelessly transmitting the RF signal output from the RF transmitting unit 15.

The CCD 13 is generally driven at an imaging rate of about 2 frames per second, and the LED 11 repeats blinking in a period including at least an imaging period of the CCD 13 or stays lit up during imaging.

Provided in the inside of the pill 1 are a power receiving antenna 17 (power-supply signal receiving unit) that receives a radio signal transmitted from the receiver 2, a separating circuit 18 (separating unit) that separates a power-supply signal from the signal received by the receiving antenna 17, a power recovering circuit 19 (power recovering unit) that recovers power from the power-supply signal, a level determining circuit 20 (reception strength determining unit) that determines the level of the power recovered and sends out the result of determination to the RF transmitting unit 15, a boosting circuit 21 that boosts the power recovered, a capacitor 22 (power accumulating unit) that stores the power boosted, and a system control circuit 23 (function executing unit, system controller) that controls the units of the pill 1 such as the CCD 13 and LED 11 by the power stored in the capacitor 22. The LED 11, the CCD 13, the RF transmitting unit 15, and the system control circuit 23 perform predetermined functions of the pill 1 to acquire in-vivo information on the body of a patient.

The CCD 13 sends out an image of the body of the patient acquired by illumination light emitted from the LED 11 that is the light emitting element, as an imaging signal that is an in-vivo information signal, to the RF transmitting unit 15. The RF transmitting unit 15 modulates the in-vivo information signal sent out from the CCD 13 to be wirelessly transmitted to the outside of the pill 1 through the RF antenna 16 that is a transmitting antenna.

An analog-to-digital converter (ADC) may be provided in a subsequent stage of the CCD 13, AD-convert the in-vivo information signal to obtain a digital signal, and wirelessly transmit the digital signal. The CCD 13 is an example of the sensor that acquires in-vivo information and further an example of the imaging unit that captures images as in-vivo information, but instead of the unit, the CCD 13 may be another imaging element such as a complementary metal oxide semiconductor (CMOS) sensor or may be some other type of sensor that acquires not information as an image of a body cavity but another body information such as temperature information and pH information.

The power receiving antenna 17 is formed with a single coil member, and receives power supply radio waves sent out from the receiver 2. After the power receiving antenna 17 receives the power supply radio waves, the separating circuit 18 separates a power-supply signal from the power supply radio waves, the power recovering circuit 19 recovers the power-supply signal as power, and the boosting circuit 21 causes the capacitor 22 to store it as power.

The capacitor 22 ensures a capacity to the extent that the pill 1 functions without a hitch even if the power supply is interrupted caused by a state where power reception is disabled, continuously for about 10 minutes, according to the orientation of the power receiving antenna 17 with respect to the respective power supply antennas of the receiver 2 (relative orientation of the antennas). Note that by fully charging the capacitor 22 in advance before the pill 1 is inserted into the body BDY of the patient, deficiency is suppressed if the power supply is interrupted for a longer time.

The system control circuit 23 controls the drive of the units such as the LED 11 and the CCD 13 by using the power stored in the capacitor 22, and controls a power supply state for causing the units to drive. A level determining signal sent out from the level determining circuit 20 to the RF transmitting unit 15 is wirelessly transmitted to the outside of the pill 1 in the same manner as that of the in-vivo information signal. The RF transmitting unit 15 wirelessly transmits the level determining signal at timing except when the in-vivo information signal is wirelessly transmitted. Therefore, an increase in power consumption can be suppressed and consumption of power stored in the capacitor 22 can also be suppressed. By wirelessly transmitting the in-vivo information intermittently, power consumption can be further suppressed.

There is a case where control information signals (drive control signal) for controlling various functions of the pill 1 are superposed on the power-supply signal by the receiver 2 to be transmitted. Therefore, a control information detecting circuit 24 (control signal detecting unit) is provided. The control information detecting circuit 24 is input with the control information signals that have been superposed on the power-supply signal and that are separated from the power-supply signal in the separating circuit 18. The control information detecting circuit 24 controls the units of the pill 1 according to the control information signals input. In other words, the control information detecting circuit 24 detects the control information signals superposed on the power-supply signal that is supplied from the receiver 2, and controls the drive of the LED 11, the CCD 13, the RF transmitting unit 15, and the system control circuit 23 based on the control information signals.

Figure 3:
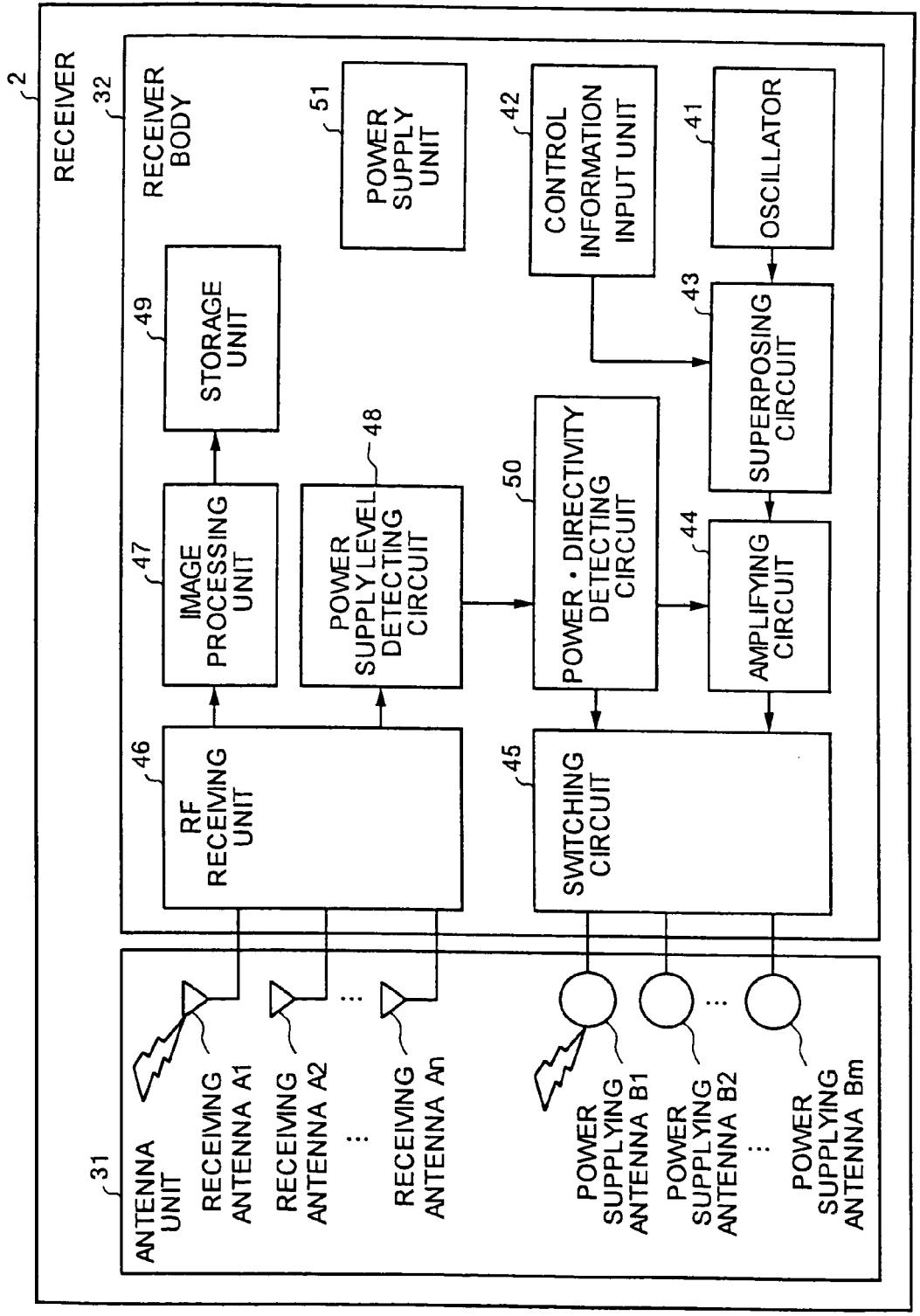
FIG. 3 is a block diagram of a receiver according to the embodiment of the present invention.
Figure 4:
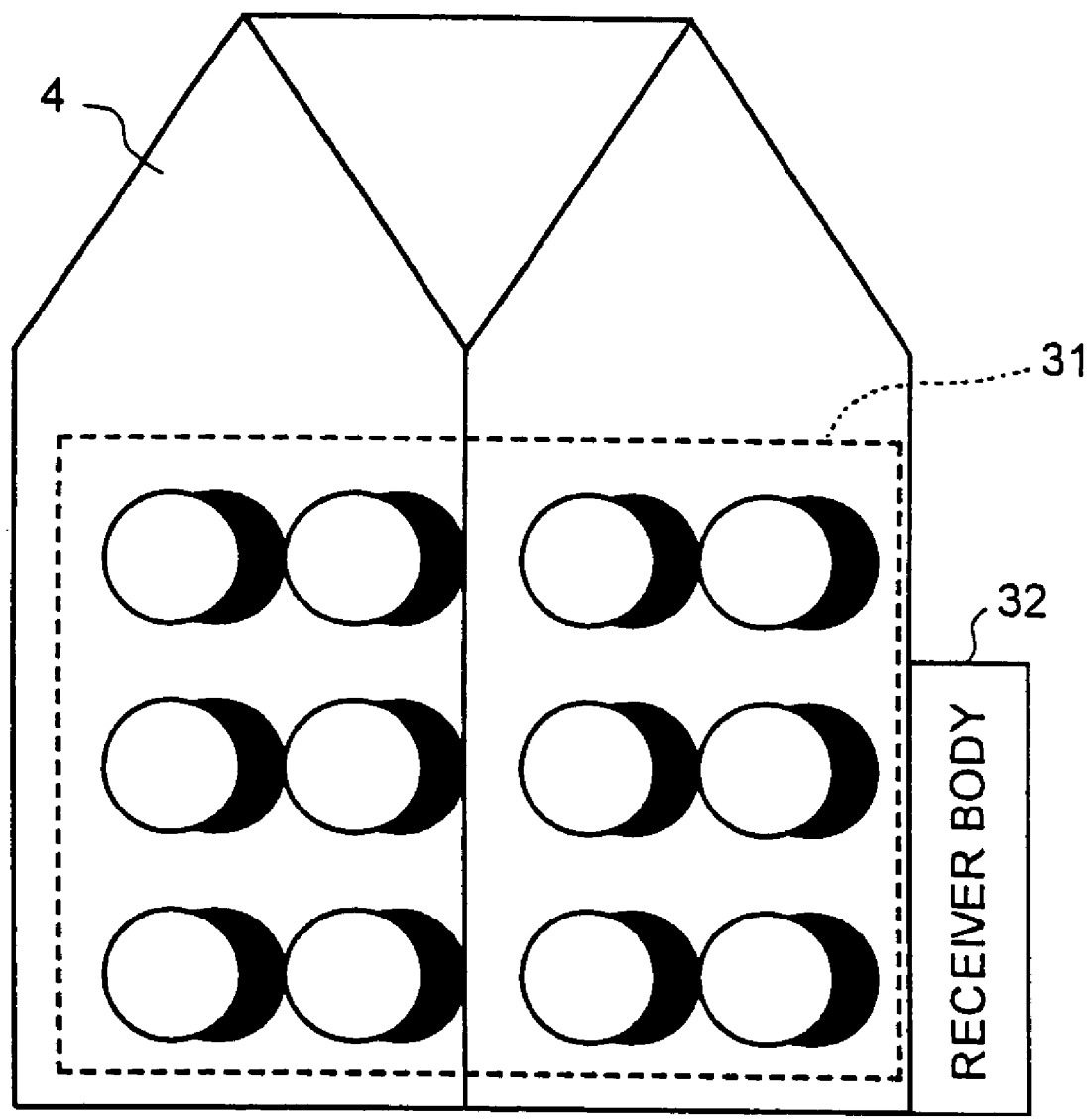
FIG. 4 is an external view of the receiver according to the embodiment of the present invention.
Figure 5:
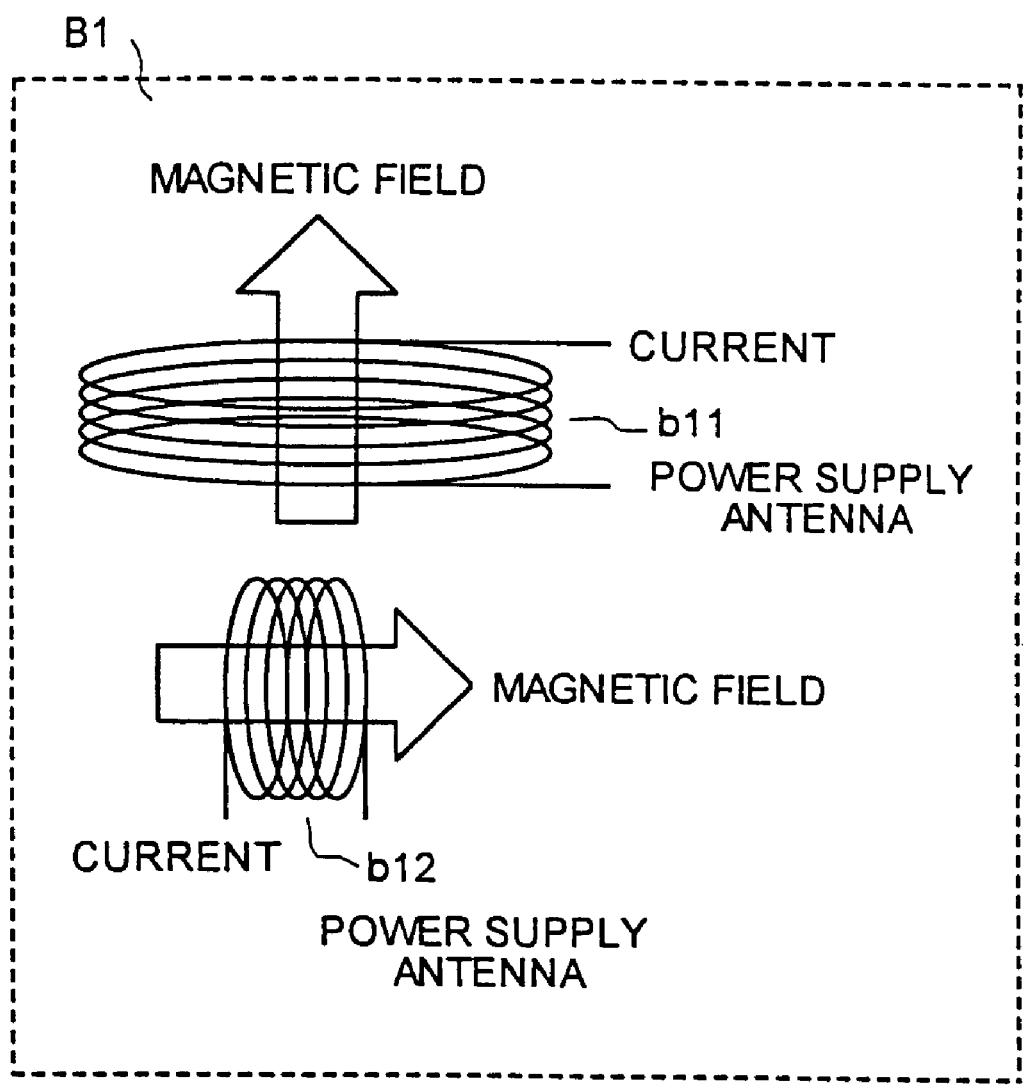
FIG. 5 is a schematic for explaining a power supply antenna of the receiver according to the embodiment of the present invention.
Figure 6:
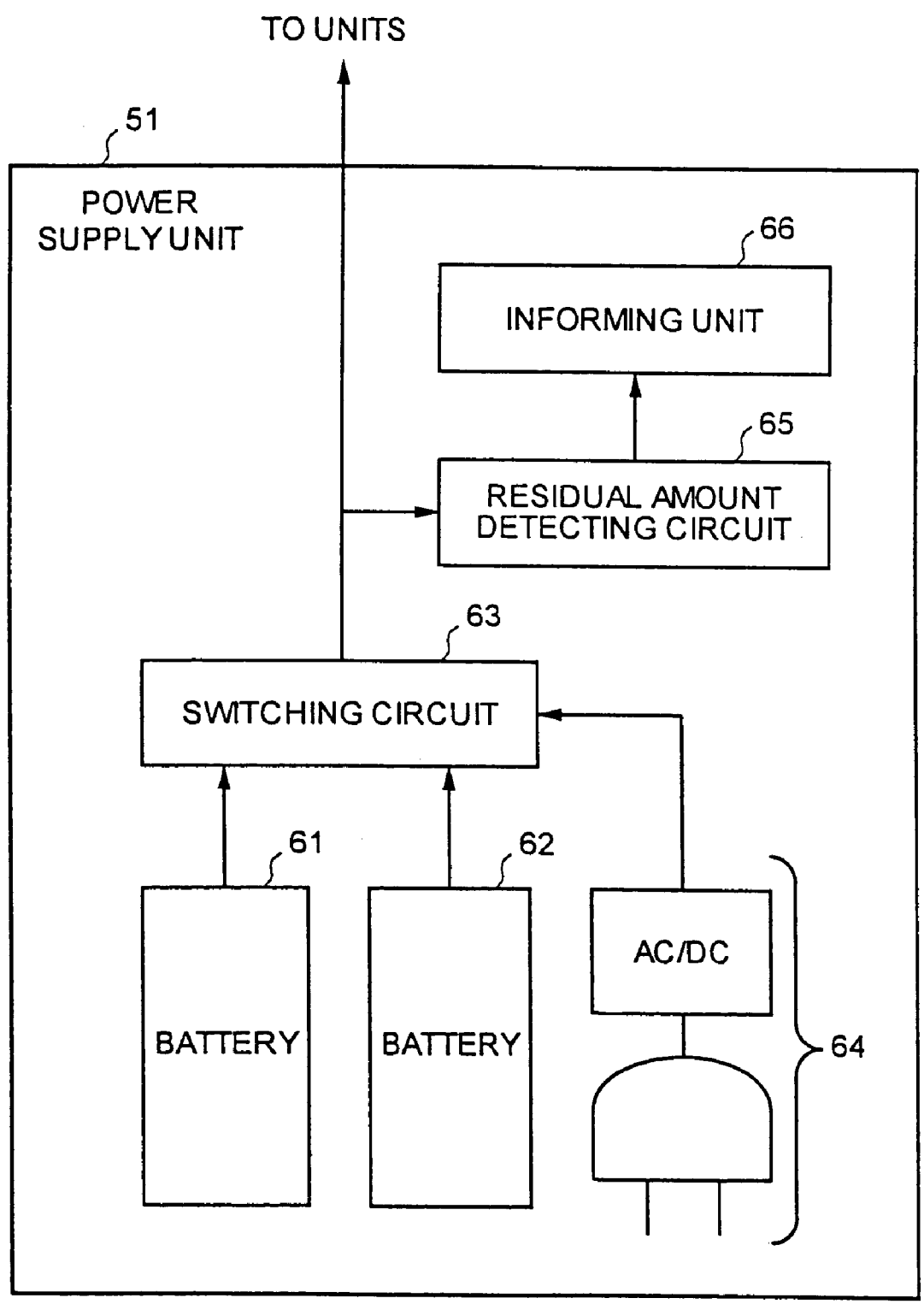
FIG. 6 is a block diagram of a power supply unit for supplying power to each unit of the receiver according to the embodiment of the present invention.

FIG. 3 is a block diagram of a receiver according to the embodiment of the present invention; FIG. 4 is an external view of the receiver according to the embodiment of the present invention; FIG. 5 is a schematic for explaining a power supply antenna of the receiver according to the embodiment of the present invention; and FIG. 6 is a block diagram of a power supply unit for supplying power to each unit of the receiver according to the embodiment of the present invention.

As shown in FIG. 3, the receiver 2 includes an antenna unit 31 that performs communications with the pill 1, and a receiver body 32 that handles information to be communicated with the pill 1 through the antenna unit 31. In the present embodiment, a case where the receiver 2 is put on a vest is shown as an example.

The antenna unit 31 includes a plurality of receiving antennas A1 to An and a plurality of power supply antennas B1 to Bm, where n and m are positive integers. The antennas of the antenna unit 31 are arranged at predetermined positions on the outer surface of the body BDY of the patient when they are put on the body. Particularly, when body information is to be acquired from any portion of stomach, small bowel, and large bowel, or all of the portions, through esophageal of the body of the patient, the antenna unit 31 is put over the breast or the abdominal portion of the body of the patient, or over the breast to the abdominal portion.

The receiver body 32 includes an oscillator 41 (power source) that generates a power-supply signal. The receiver body 32 also includes a control information input unit 42 (control signal input unit) that receives control information with which an operator controls the functions of the pill 1. Some information can be input from the control information input unit 42.

In the present embodiment, the following information and the system control circuit 23 are controlled. That is, the information includes information for changing the number of frames that is an imaging rate of the CCD 13, i.e., information for changing the number of frames of images to be captured within a predetermined time, and information on LED light-up time that changes the light-up time of the LED 11 and the timing of lighting it up. By controlling these, a power source ON/OFF information is input from the control information input unit 42. The power source ON/OFF information is used to switch between an active mode in which supplying the power to the units causes acquisition of in-vivo information to be executed and a standby mode in which suppressing the power to the units causes acquisition of in-vivo information to be postponed.

Provided in the subsequent stage of the oscillator 41 is a superposing circuit 43. The superposing circuit 43 (control signal superposing unit) superposes the control information input from the control information input unit 42 on the power-supply signal output from the oscillator 41. Next, the power-supply signal with the control information superposed thereon is amplified by an amplifying circuit 44 provided in the subsequent stage of the superposing circuit 43 and is output to a switching circuit 45. An amplifying factor of the power-supply signal in the amplifying circuit 44 is changeable. The power-supply signal input to the switching circuit 45 is wirelessly transmitted from the power supply antenna of the antenna unit 31.

It is assumed that an instruction to change the imaging rate of the CCD 13 from a first imaging rate to a second imaging rate is input from the control information input unit 42. An information signal for changing the number of frames sent out from the control information input unit 42 is superposed on the power-supply signal in the superposing circuit 43 to be input to the amplifying circuit 44. Further, the information signal superposed on the power-supply signal is amplified at a predetermined amplifying factor in the amplifying circuit 44, is sent out to an optimal power supply antenna of the power supply antennas B1 to Bm in the switching circuit 45, and is wirelessly transmitted from the power supply antenna.

The power-supply signal thus wirelessly transmitted is received by the power receiving antenna 17 of the pill 1 as explained above. The information signal for changing the number of frames that is the control information signal separated from the power-supply signal in the separating circuit 18 is input to the control information detecting circuit 24. Here, a frequency band of the control information signal is made different from that of the power-supply signal, and the frequency band of the control information signals is changed to another one depending on the contents for control.

By thus doing, the control information signal can be wirelessly transmitted as a multiple signal from the receiver 2. Further, in the pill 1, the separating circuit 18 can separate the signals input from each other based on the frequency bands, and the control information detecting circuit 24 can detect the contents of the control information. The control information detecting circuit 24 with the control information signal input detects it as the information signal for changing the number of frames, and controls the CCD drive circuit 14 so as to drive the CCD 13 according to the contents for control (change from the first imaging rate to the second imaging rate).

When the LED 11 is configured to blink during an imaging period of the CCD 13, a control signal may be transmitted from the control information detecting circuit 24 to the LED drive circuit 12 so as to automatically change the light-up period from a first light-up period, which is a present light-up period, to a second light-up period, which is suitable for the second imaging rate, according to the imaging rate of the CCD 13 changed by the contents for control (change from the first imaging rate to the second imaging rate).

If the control information detected by the control information detecting circuit 24 is the power source ON/OFF information which causes to switch between the active mode in which supplying the power to the units causes acquisition of in-vivo information to be executed and the standby mode in which suppressing the power to the units causes acquisition of in-vivo information to be postponed, the control information detecting circuit 24 sends out the control signal to the system control circuit 23 to control the control signal so as to switch between the modes.

The superposing circuit 43 continues superposing the same control information on the power-supply signal within at least a predetermined period unless new information is input from the control information input unit 42. By thus doing, the pill 1 can receive the control information even if the pill 1 cannot temporarily receive it in some period. As explained above, the functions of the pill 1 after being inserted into the body BDY of the patient can be wirelessly controlled from the outside, which prevents acquisition of in-vivo information on an unnecessary portion of the body of the patient too much or prevents careless power consumption.

It is preferable that the antenna unit 31 is previously provided on clothes such as a vest 4 that is easily put on and taken off, as shown in FIG. 4. If the antenna unit 31 is provided on such a vest 4, the patient just puts on this vest 4, and the antennas are thereby easily arranged at most appropriate positions with respect to the body BDY of the patient.

Although the antenna unit 31 is provided on the outside surface of the vest 4 in the case of FIG. 4, it may also be provided on the rear side thereof. Alternatively, by using, for example, Magic Tape (trademark), the antennas are made to be removable from the antenna unit 31, and therefore, the arrangement of the antennas may be changed as required according to a purpose of performing examination (a portion to be particularly observed). It is noted that the vest 4 has a shield material (not shown) provided on the outside surface of the vest 4 so that electromagnetic waves from the outside are not received by the antennas of the antenna unit 31, that is, the antennas receive only signals sent out from the inside of the body BDY of the patient.

The receiving antennas A1 to An are connected to an RF receiving unit 46 of the receiver body 32. The power supply antennas B1 to Bm are connected to the switching circuit 45. Furthermore, the receiving antennas A1, A2, . . . , An are superposed on the power supply antennas B1, B2, . . . , Bm, respectively, and each antenna pair superposed on each other is arranged on the same position with respect to the body BDY of the patient. Therefore, in the present embodiment, a relation of n=m is obtained.

As shown in FIG. 5, the power supply antenna B1 includes power supply antennas b11 (first power-supply signal transmitting unit) and b12 (second power-supply signal transmitting unit) that are two coil members having different directivities and are disposed so that an angle of 90° is formed between directions of magnetic fields that are produced through energization thereto. Because of this configuration, deficiency such that power supply is not satisfactorily performed depending on an orientation of the power receiving antenna 17 of the pill 1 is resolved. Likewise, the power supply antenna B2 includes power supply antennas b21 and b22 that are two coil members, and the same configuration is also included in the power supply antenna B3 and thereafter. The power supply antenna Bm includes power supply antennas bm1 and bm2.

By causing the switching circuit 45 to operate, the power supply antennas that receive the power-supply signals and send out power supply radio waves to be sequentially switched to the power supply antennas b11, b12, the power supply antennas b21, b22, . . . , and the power supply antennas bm1 and bm2 in each predetermined time.

Although the power supply antenna includes the two coil members having directivities along two directions, provision of one more coil member so that the direction of its magnetic field is orthogonal to the directions of the magnetic fields of the other two coil members may cause the power supply antenna to have directivities along three directions.

The receiving antennas A1 to Am receive the in-vivo information signals and the level determining signals wirelessly transmitted from the pill 1, respectively, and all the signals received are input to the RF receiving unit 46. The RF receiving unit 46 is configured to demodulate the input in-vivo information signals and level determining signals. The subsequent stage of the RF receiving unit 46 is connected with an image processing unit 47 and a power supply level detecting circuit 48. The former that is the image processing unit 47 is input with the in-vivo information signals demodulated in the RF receiving unit 46, while the latter that is the power supply level detecting circuit 48 is input with a signal for detecting a power supply level from the RF receiving unit 46.

The image processing unit 47 to which the in-vivo information signals are input performs a predetermined process so that the in-vivo information signal is subjected to imaging and an imaging signal is output. The subsequent stage of the image processing unit 47 is connected with a storage unit 49 such as a built-in type hard disk drive and a portable type CompactFlash (trademark) memory, which stores the imaging signal.

On the other hand, the power supply level detecting circuit 48 sequentially switches between the power supply antennas in the above-mentioned manner to detect how the power to the capacitor 22 of the pill 1 is supplied by the power supply radio waves transmitted from the power supply antennas, based on the respective level determining signals that the pill 1 sequentially generates and transmits. The power supply level detecting circuit 48 detects the power supply levels each indicating the supplied power by receiving the radio waves, wirelessly transmitted from the power supply antennas, by the receiving antenna 17 of the pill 1.

A power-directivity detecting circuit 50 provided in the subsequent stage of the power supply level detecting circuit 48 decides an amplifying factor of power supply radio waves in the amplifying circuit 44 based on the results of detection in the power supply level detecting circuit 48, and sends out a control signal so as to cause the switching circuit 45 to select a power supply antenna that is capable of performing the most effective power supply. The amplifying circuit 44 performs an amplifying operation so as to amplify the power supply radio waves up to a predetermined adequate level that has been previously set, according to the control signal transmitted from the power-directivity detecting circuit 50. The switching circuit 45 switches to a power supply antenna that is possible to perform the most effective power supply, according to the control signal sent out from the power-directivity detecting circuit 50. In this case, if the power supply antenna b11 has a signal strength higher than that of the power supply antenna b12 based on the result of detection in the power supply level detecting circuit 48, the switching circuit 45 may be controlled so as to output a power-supply signal only from the power supply antenna b11.

For example, it is assumed that the level determining circuit 20 of the pill 1 determines power by setting strength of the power to five levels according to the magnitude of the strength. The five levels are divided into those as follows: 5: maximum, 4: high, 3: adequate, 2: low, 1: slight. Since different values are set previously for respective levels in order to determine the five levels, the strength is determined by comparing each of the values with the strength of power. Assume that only in the case of sending out the radio waves from the power supply antenna b11, "5" is determined as the result of determination by the level determining circuit 20, and that only in the case of sending out the radio waves from another power supply antenna, "4" or below is determined as the result of determination. Then, for suppressing consumption of the battery in the receiver 2 and effectively supplying power, the power directivity detecting circuit 50 sends out a control signal, for causing the amplifying circuit 44 to set an amplifying factor so that the result of determination by the level determining circuit 20 becomes "3", to the switching circuit 45. The power directivity detecting circuit 50 further sends out a control signal for selecting the power supply antenna b11 to the switching circuit 45.

If the result of determination is "2" or below even if the radio waves are sent out from any of the power supply antennas, the power directivity detecting circuit 50 controls the switching circuit 45 so as to sequentially switch between the power supply antennas, and controls the amplifying circuit 44 so as to increase the amplifying factor until a power supply antenna for obtaining the result of determination of "3" is detected.

Although the result of determination in the level determining circuit 20 includes the five levels for convenience as explained above, it is not limited to five, and therefore, the levels may be less than or more than the five levels.

The receiver 2 includes a power supply unit 51 that supplies power to the units. The power supply unit 51 is configured as shown in FIG. 6. The power supply unit 51 includes a switching circuit 63 that selects a power source from which power is supplied, of a plurality of power sources. The plurality of power sources are a main battery 61, a spare battery 62, and an AC power source 64 that are removably connected to the switching circuit 63.

The power supply unit 51 also includes a residual amount detecting circuit 65 that detects a residual amount of a battery selected as the power source from the power input through the switching circuit 63, and an informing unit 66, such as an LED and a speaker, that informs the result of detection in the residual amount detecting circuit 65. These components are provided in the subsequent stage of the switching circuit 63.

The residual amount detecting circuit 65 outputs a signal to the informing unit 66 that blinks the LED or outputs sounds by always detecting how the residual amount of the battery is like, or in response to detection that the residual amount of the battery connected to the switching circuit 63 is close to a predetermined value such as 0 (zero). The operation of the informing unit 66 allows the residual amount of the battery to be informed to an operator. Alternatively, if a plurality of power sources is connected to the switching circuit 63, the switching circuit 63 selects the AC power source 64, the battery 61, and the battery 62 in this preferential order.

When it is detected that the residual amount of the battery is close to the predetermined value such as 0 (zero) as the result of detecting the residual amount of the battery in the residual amount detecting circuit 65, this information may be fed back to the switching circuit 63 to cause it to perform switching operation so as to switch to a battery having the next priority.

When the AC power source 64 is connected to the switching circuit 63, the batteries may be charged simultaneously when power is supplied to the units. When the AC power source 64 is connected thereto, the switching circuit 63 may cause a power supply preferentially from the AC power source 64.

As explained above, according to the present embodiment, it is possible to realize a power supply to the device, such as the pill, that is insertable into the body of a patient (body-insertable device), and control a function desired by an operator of the body-insertable device. As a result, usability can be improved.

Although the capsule-type endoscope system is explained as an example, the body-insertable device is not necessarily limited to this, and changes may be applicable without departing from the spirit and scope of the present invention. In other words, not only the body-insertable device measures the information on the inside of the body of the patient to acquire the image of the inside of the body, but also it can be applied to a overall system to measure pH information, temperature information, and pressure information by providing a pH sensor, a temperature sensor, and a pressure sensor in the pill, respectively.

As explained above, according to the present invention, it is advantageous to provide the wireless in-vivo information acquiring system with improved usability capable of realizing a power supply to the device, such as the pill, that is insertable into the body of a patient (body-insertable device), and controlling a function desired by an operator of the body-insertable device, a body-insertable device, and an external device.

Although the invention has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth.

What is claimed is:

1. A wireless in-vivo information acquiring system comprising:
   a body-insertable device that is inserted into a body of a patient; and
   an external device that is disposed on outside of the body of the patient, wherein
   the external device includes
      a power source that outputs a power-supply signal for supplying power to the body-insertable device;
      a power supply signal transmitting unit that wirelessly supplies the power supply signal from the power source to the body-insertable device; and
      a control signal superposing unit that superposes a drive control signal on the power supply signal from the power source, the drive control signal indicating whether to request in-vivo information, and
   the body-insertable device includes
      a function executing unit that executes a predetermined function to acquire in-vivo information on the body of the patient;
      a separating unit that separates the drive control signal from the power supply signal;
      a power accumulating unit that receives the power supply signal after the separating unit separates the drive control signal;
      a control signal detecting unit that detects the drive control signal superposed on the power supply signal; and
      a system controller that controls the function executing unit to execute the predetermined function while supplying power accumulated in the power accumulating unit to the function executing unit when the drive control signal indicates a request for in-vivo information, and stops supplying the power to the function executing unit when the drive control signal does not indicate the request for in-vivo information;
   wherein the body-insertable device further includes a level determining unit that determines a level of power of the power supply signal transmitted from the external device to transmit a level determining signal indicating the level of power to the external device and the external device further includes a power supply level detecting unit that detects the level determining signal and a power directivity detecting unit that amplifies the power-supply signal to be transmitted to the body-insertable device, based on the level determining signal.

2. The wireless in-vivo information acquiring system according to claim 1, wherein the external device further includes a control information input unit that outputs the drive control signal upon receiving control information about controlling the function executing unit.

3. The wireless in-vivo information acquiring system according to claim 1, wherein
   the power supply signal has a first frequency band,
   the drive control signal has a second frequency band that is different from the first frequency band, and
   the separating unit separates the power supply signal from the drive control signal by separating a signal in the first frequency band from a signal in the second frequency band.

4. The wireless in-vivo information acquiring system according to claim 1, wherein the function executing unit is a sensor that acquires in-vivo information specific to a portion to be diagnosed in the body of the patient.

5. The wireless in-vivo information acquiring system according to claim 4, wherein the function executing unit includes an imaging unit that captures an image of the portion to be diagnosed in the body of the patient, the control information received by the control information input unit includes information on number of frames to be captured by the imaging unit per predetermined time, and the drive control signal output from the control information input unit includes a signal for controlling the number of frames to be captured by the imaging unit per predetermined time.

6. The wireless in-vivo information acquiring system according to claim 5, wherein the function executing unit includes an illuminating unit that emits light to illuminate at least the portion to be diagnosed in the body of the patient, the control information received by the control information input unit includes information on emission time of the illuminating unit, and the drive control signal output from the control information input unit includes a signal for controlling the emission time of the illuminating unit.

7. A body-insertable device comprising:

a function executing unit that executes a predetermined function to acquire in-vivo information on the body of the patient;

a power-supply signal receiving unit that receives a power-supply signal wirelessly transmitted from outside as a power for driving the function executing unit, the power-supply signal including a drive control signal indicating whether to request in-vivo information, superposed thereon;

a separating unit that separates the drive control signal from the power supply signal;

a power accumulating unit that receives the power supply signal after the separating unit separates the drive control signal;

a control signal detecting unit that detects the drive control signal superposed on the power supply signal received;

a system controller that controls the function executing unit to execute the predetermined function while supplying power accumulated in the power accumulating unit to the function executing unit when the drive control signal indicates a request for in-vivo information, and stops supplying the power to the function executing unit when the drive control signal does not indicate the request for in-vivo information; and a level determining unit that determines a level of power supply signal to transmit a level determining signal indicating the level of power to outside.

8. The body-insertable device according to 7, wherein the power supply signal has a first frequency band, the drive control signal has a second frequency band that is different from the first frequency band, and the separating unit separates the power supply signal from the drive control signal by separating a signal in the first frequency band from a signal in the second frequency band.

9. The body-insertable device according to claim 7, wherein the function executing unit is a sensor that acquires in-viva information specific to a portion to be diagnosed in the body of the patient.

10. The body-insertable device according to claim 9, wherein the function executing unit includes an imaging unit that captures an image of the portion to be diagnosed in the body of the patient, control information received by a control information input unit of an external device includes information on number of frames to be captured by the imaging unit per predetermined time, and the drive control signal output from the control information input unit includes a signal for controlling the number of frames to be captured by the imaging unit per predetermined time.

11. The body-insertable device according to claim 10, wherein the function executing unit includes an illuminating unit that emits light to illuminate at least the portion to be diagnosed in the body of the patient, the control information includes information on emission time of the illuminating unit, and the drive control signal output from the control information input unit includes a signal for controlling the emission time of the illuminating unit.

12. An external device comprising:

a power source that outputs a power-supply signal for supplying power to a body-insertable device that is inserted into a body of a patient to execute a predetermined function;

a control signal superposing unit that superposes a drive control signal for controlling the predetermined function of the body-insertable device on the power supply signal from the power source, the drive control signal indicating whether to request in-vivo information;

a power supply signal transmitting unit that wirelessly supplies the power supply signal from the power source to the body-insertable device that is inserted into the body, the power-supply signal including the drive control signal superposed;

a power supply level detecting unit that detects a level determining signal transmitted from the body-insertable device, the level determining signal indicating a level of power that the body-insertable device has received through the power supply signal; and a power directivity detecting unit that amplifies the power-supply signal to be transmitted to the body-insertable device, based on the level determining signal.

13. The external device according to claim 12, further comprising a control information input unit that outputs the drive control signal upon receiving control information about controlling a function executing unit of a body-insertable device.

14. The external device according to claim 12, wherein the power supply signal has a first frequency band, and the drive control signal has a second frequency band that is different from the first frequency band.

* * * * *